(12) United States Patent
Goncalves Filho et al.

(10) Patent No.: US 9,427,387 B2
(45) Date of Patent: Aug. 30, 2016

(54) COLOR-STABLE ORAL CARE COMPOSITIONS

(71) Applicant: Colgate-Palmolive Company, New York, NY (US)

(72) Inventors: Luiz Alberto Goncalves Filho, Sao Paulo (BR); Raquel Margutti Olivi, Sao Paolo (BR); Rensl Dillon, Ewing, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 14/647,306

(22) PCT Filed: Nov. 30, 2012

(86) PCT No.: PCT/US2012/067342
§ 371 (c)(1),
(2) Date: May 26, 2015

(87) PCT Pub. No.: WO2014/084851
PCT Pub. Date: Jun. 5, 2014

(65) Prior Publication Data
US 2015/0306000 A1    Oct. 29, 2015

(51) Int. Cl.
| | | |
|---|---|---|
| A61K 8/46 | (2006.01) |
| A61K 8/31 | (2006.01) |
| A61Q 11/00 | (2006.01) |
| C09B 67/22 | (2006.01) |

(52) U.S. Cl.
CPC . *A61K 8/46* (2013.01); *A61K 8/31* (2013.01); *A61K 8/466* (2013.01); *A61Q 11/00* (2013.01); *C09B 67/0041* (2013.01); *A61K 2800/40* (2013.01); *A61K 2800/42* (2013.01); *A61K 2800/43* (2013.01)

(58) Field of Classification Search
USPC .......................................................... 424/49
See application file for complete search history.

(56) References Cited

U.S. PATENT DOCUMENTS

| | | | |
|---|---|---|---|
| 4,132,770 A | 1/1979 | Barth | |
| 4,895,720 A * | 1/1990 | Ladas | A61K 8/25 424/49 |
| 2002/0197215 A1 | 12/2002 | Stier | |
| 2005/0163729 A1 | 7/2005 | Zaidel et al. | |
| 2012/0264078 A1 | 10/2012 | Patel et al. | |
| 2013/0272971 A1 | 10/2013 | Pimenta et al. | |
| 2013/0330283 A1 | 12/2013 | Vogt et al. | |

FOREIGN PATENT DOCUMENTS

| | | |
|---|---|---|
| EP | 0208009 | 6/1991 |
| EP | 0287074 | 11/1993 |
| WO | WO 97/21418 | 6/1997 |
| WO | WO 2004/073672 | 9/2004 |
| WO | WO 2006/052593 | 5/2006 |
| WO | WO2012/087325 | 6/2012 |

OTHER PUBLICATIONS

International Search Report and Written Opinion in International Application PCT/US2012/067342, mailed Sep. 2, 2013.
Lachman et al., 2006, "Color stability of tablet formulations II. Influence of light intensity on the fading of several water-soluble dyes," J. American Pharmaceutical Assoc. 49(3):165-169.

* cited by examiner

*Primary Examiner* — Walter Webb

(57) ABSTRACT

Disclosed herein are oral care compositions comprising a colorant blend comprising a triarylmethane green colorant and a naphthalene sulfonate yellow colorant in a weight ratio of from 2:1 to 1:2; and a substituted or unsubstituted phenyl alkene flavorant.

25 Claims, No Drawings

COLOR-STABLE ORAL CARE COMPOSITIONS

BACKGROUND

In order to provide consumer acceptance, many oral care compositions, such as mouthwashes, mouth rinses and dentifrices, have flavorant(s) and colorant(s) added to the active components of the composition to impart a desired flavor and color to the oral care composition. It is important to the consumer that the color and flavor are constant both from batch to batch and so that the color and flavor do not perceptibly change over time, either as a result of storage conditions in the supply chain before purchase or as a result of use and storage conditions after purchase.

In some instances the flavorant and colorant components can interact over time, leading to a readily perceptible change over time in the flavor and/or color of the composition.

There is therefore a need to provide an oral care composition having color stability when a particular color is combined with a particular flavor.

SUMMARY

The present invention aims at least partially to meet this need in the art. Further embodiments of the invention will be apparent from the detailed description and the examples.

In some embodiments, the present invention provides an oral care composition comprising: a triarylmethane green colorant and a naphthalene sulfonate yellow colorant in a weight ratio of from 2:1 to 1:2; and a substituted or unsubstituted phenyl alkene flavorant.

In other embodiments, the present invention provides an oral care composition comprising a colorant blend including a triarylmethane green colorant and a naphthalene sulfonate yellow colorant in a weight ratio of from 2:1 to 1:2 to provide a green color to the oral care composition and a flavorant blend including a substituted or unsubstituted phenyl alkene flavorant.

Optionally, the triarylmethane green colorant comprises FD & C Green No. 3 colorant. Optionally, the naphthalene sulfonate yellow colorant comprises FD & C Yellow No. 6 colorant.

Optionally, the triarylmethane green colorant and the naphthalene sulfonate yellow colorant are present in a weight ratio of from 1.5:1 to 1:1.5, further optionally from 1.25:1 to 1:1, yet further optionally about 1.2:1.

Optionally, the triarylmethane green colorant is present in an amount of from 0.00025 to 0.00075 wt % and the naphthalene sulfonate yellow colorant is present in an amount of from 0.00025 to 0.00075 wt %, each based on the total weight of the composition. Further optionally, the triarylmethane green colorant is present in an amount of from 0.00035 to 0.00055 wt % and the naphthalene sulfonate yellow colorant is present in an amount of from 0.00030 to 0.00045 wt %, each based on the total weight of the composition. Yet further optionally, the triarylmethane green colorant is present in an amount of from 0.00040 to 0.00050 wt % and the naphthalene sulfonate yellow colorant is present in an amount of from 0.00030 to 0.00040 wt %, each based on the total weight of the composition.

Optionally, the substituted or unsubstituted phenyl alkene flavorant comprises an unsaturated phenyl ether. Typically, the unsaturated phenyl ether comprises anethole.

Optionally, the substituted or unsubstituted phenyl alkene flavorant is present in a weight ratio of from 8:1 to 4:1, further optionally about 6:1, with respect to the colorant blend.

Optionally, the substituted or unsubstituted phenyl alkene flavorant is present in an amount of from 0.003 to 0.007 wt %, further optionally from 0.004 to 0.006 wt %, yet further optionally from 0.0045 to 0.0050 wt %, based on the total weight of the composition.

Optionally, the oral care composition may further comprise a pH adjuster to adjust the pH of the composition and the pH of the composition is from 4.60 to 5.60. Typically, the pH of the composition is about 5.10.

Typically, the pH adjuster comprises an organic acid, for example citric acid. Optionally, the organic acid is present in an amount of from 0.005 to 0.015 wt %, further optionally from 0.008 to 0.012 wt %, based on the total weight of the composition.

Optionally, the green color has a delta E of less than 2 when exposed to an accelerated aging test comprising ambient daylight conditions and a temperature of 40° C. for a period of 4 weeks.

Optionally, the oral care composition is a mouthwash or mouthrinse.

The invention further provides the use, in an oral care composition according to the invention and comprising a colorant blend to provide a green color to the oral care composition and a flavorant blend including a substituted or unsubstituted phenyl alkene flavorant, of a triarylmethane green colorant and a naphthalene sulfonate yellow colorant in a weight ratio of from 2:1 to 1:2 to stabilize the green color and provide a delta E of less than 2 when the oral care composition is exposed to an accelerated aging test comprising ambient daylight conditions and a temperature of 40° C. for a period of 4 weeks.

DETAILED DESCRIPTION

It should be understood that the detailed description, and specific examples, while indicating embodiments of the invention, are intended for purposes of illustration only and are not intended to limit the scope of the invention.

As used throughout, ranges are used as shorthand for describing each and every value that is within the range. Any value within the range can be selected as the terminus of the range.

As used herein, the words "optionally", "typically", "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the term "about," when applied to the value for a parameter of a composition or method of this invention, indicates that the calculation or the measurement of the value allows some slight imprecision without having a substantial effect on the chemical or physical attributes of the composition or method. If, for some reason, the imprecision provided by "about" is not otherwise understood in the art with this ordinary meaning, then "about" as used herein indicates a possible variation of up to 5% in the value.

As referred to herein, all compositional percentages are by weight of the total composition, unless otherwise specified.

In some embodiments, the present invention provides an oral care composition comprising: a triarylmethane green colorant and a naphthalene sulfonate yellow colorant in a weight ratio of from 2:1 to 1:2; and a substituted or unsubstituted phenyl alkene flavorant.

In some embodiments, the invention provides an oral care composition comprising an oral care composition comprising a colorant blend including a triarylmethane green colorant and a naphthalene sulfonate yellow colorant in a weight ratio of from 2:1 to 1:2 to provide a green color to the oral care composition and a flavorant blend including a substituted or unsubstituted phenyl alkene flavorant.

The invention relates to oral care compositions generally which are to present a green colored appearance to the user, but in particular embodiments relates to mouthwashes and mouth rinses.

As discussed further in detail below, the invention is predicated on the finding by the inventors that the selection of a combination of particular green and yellow colorants can reduce the tendency of an oral care composition to color fading during extended storage and use when the oral care composition comprises a particular flavorant which tends to induce such color fading when other colorants or colorant blends are present.

In some embodiments, the green color has a delta E of less than 2 when exposed to an accelerated aging test comprising ambient daylight conditions and a temperature of 40° C. for a period of 4 weeks. The practical effect of such a low delta E value is that any color change is substantially imperceptible to the human eye.

The invention correspondingly further provides the use, in an oral care composition according to the invention and comprising a colorant blend to provide a green color to the oral care composition and a flavorant blend including a substituted or unsubstituted phenyl alkene flavorant, of a triarylmethane green colorant and a naphthalene sulfonate yellow colorant in a weight ratio of from 2:1 to 1:2 to stabilize the green color and provide a delta E of less than 2 when the oral care composition is exposed to an accelerated aging test comprising ambient daylight conditions and a temperature of 40° C. for a period of 4 weeks.

In some embodiments, the triarylmethane green colorant comprises FD & C Green No. 3 colorant and/or the naphthalene sulfonate yellow colorant comprises FD & C Yellow No. 6 colorant. Typically, both FD & C Green No. 3 and FD & C Yellow No. 6 colorants are present. These colorants are widely available commercially.

FD & C Green No. 3 has the formula ethyl-[4-[[4-(ethyl-[(3-sulfophenyl) methyl] amino] phenyl]-(4-hydroxy-2-sulfophenyl) methylidene]-1-cyclohexa-2,5-dienylidene]-[(3-sulfophenyl) methyl] azanium.

The FD & C Green No. 3 Formula is:

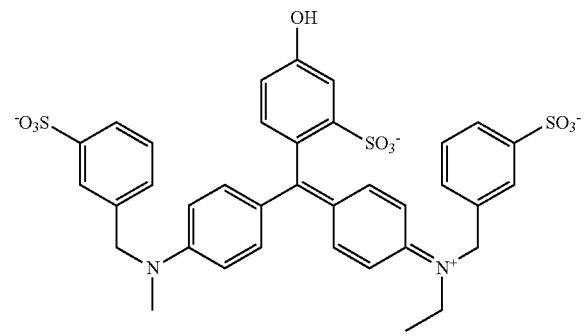

FD & C Yellow No. 6 has the formula disodium 6-hydroxy-5-[(4-sulfophenyl)azo]-2-naphthalenesulfonate.

The FD & C Yellow No. 6 Formula is:

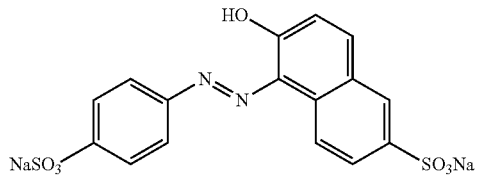

In some embodiments, the triarylmethane green colorant and the naphthalene sultanate yellow colorant are present in a weight ratio of from 1.5:1 to 1:1.5, further optionally from 1.25:1 to 1:1, yet further optionally about 1.2:1. By selecting the weight ratio, the desired green color, in particular a bright mint green, can be achieved.

In some embodiments, the triarylmethane green colorant is present in an amount of from 0.00025 to 0.00075 wt % and the naphthalene sulfonate yellow colorant is present in an amount of from 0.00025 to 0.00075 wt %, each based on the total weight of the composition. Further optionally, the triarylmethane green colorant is present in an amount of from 0.00035 to 0.00055 wt % and the naphthalene sulfonate yellow colorant is present in an amount of from 0.00030 to 0.00045 wt %, each based on the total weight of the composition. Yet further optionally, the triarylmethane green colorant is present in an amount of from 0.00040 to 0.00050 wt % and the naphthalene sulfonate yellow colorant is present in an amount of from 0.00030 to 0.00040 wt %, each based on the total weight of the composition. By selecting these colorant amounts, the desired intensity of the green color can be achieved in the oral care composition.

In some embodiments, the substituted or unsubstituted phenyl alkene flavorant is present in combination with other flavorant components to provide a flavorant blend in the composition which delivers a desired overall flavor, for example a fresh mint flavor, to the user. For example, the flavorant blend may also include spearmint oil, or any other mint flavorants, as a major component.

In some embodiments, the substituted or unsubstituted phenyl alkene flavorant comprises an unsaturated phenyl ether. Typically, the unsaturated phenyl ether comprises anethole, most typically trans-anethole.

In some embodiments, the substituted or unsubstituted phenyl alkene flavorant is present in a weight ratio of from 8:1 to 4:1, further optionally about 6:1, with respect to the colorant blend. By selecting a weight relationship between the phenyl alkene flavorant and the colorant blend, the desired color stability can conveniently be achieved.

Optionally, the substituted or unsubstituted phenyl alkene flavorant is present in an amount of from 0.003 to 0.007 wt %, further optionally from 0.004 to 0.006 wt %, yet further optionally from 0.0045 to 0.0050 wt %, based on the total weight of the composition. These amounts provide the composition with the desired flavor profile contribution by the phenyl alkene component.

FD & C Green No. 3 colorant has an absorption maximum of 625 nm. The absorption maximum of the naphthalene sulfonate yellow colorant can be pH dependent. FD & C Yellow No. 6 colorant has an absorption maximum between 480 nm and 500 nm depending upon the pH of the composition. Accordingly, in order to "tune" the overall green color of the composition to a desired hue, a pH adjuster may be present so that the maximum absorption of the naphthalene sulfonate yellow colorant is at the desired value.

Therefore, in some embodiments, the oral care composition may further comprise a pH adjuster to adjust the pH of the composition and the pH of the composition is from 4.60 to 5.60. The pH of the composition is about 5.10.

Typically, the pH adjuster comprises an organic acid, for example citric acid, although any other orally acceptable acid may alternatively or additionally be employed. In some embodiments, the organic acid is present in an amount of from 0.005 to 0.015 wt % based on the total weight of the composition. In some embodiments, the organic acid is present in an amount of from 0.008 to 0.012 wt % based on the total weight of the composition.

The oral care composition may additionally comprise a carrier, in particular any suitable carrier for the respective composition, whether the oral care composition is, for example, a mouthwash, mouth rinse or dentifrice.

Among useful carriers for optional inclusion in a composition of the invention are diluents, surfactants, foam modulators, thickening agents, viscosity modifiers, humectants, sweeteners, anticaries agents, and anticalculus or tartar control agents. Carriers should be selected for compatibility with each other and with other ingredients of the composition.

Water is a preferred diluent and in some compositions such as mouthwashes, water is commonly accompanied by an alcohol, e.g., ethanol, or alternatively the composition is alcohol-free. The weight ratio of water to alcohol in a mouthwash composition is generally 1:1 to 20:1, for example 3:1 to 20:1 or 4:1 to 10:1. In a whitening liquid, the weight ratio of water to alcohol can be within or below the above ranges, for example, 1:10 to 2:1.

In a still further embodiment, in addition to any pH adjuster, the composition of the invention may comprise at least one buffering agent to control pH within a desired range. Any pH adjusting or buffering agents are optionally present in a total amount effective to maintain the composition in an orally acceptable pH range.

In a still further embodiment, the composition of the invention comprises at least one surfactant. Any orally acceptable surfactant, most of which are anionic, nonionic or amphoteric, can be used. Suitable anionic surfactants include without limitation, water-soluble salts of $C_{8-20}$ alkyl sulfates, sulfonated monoglycerides of $C_{8-20}$ fatty acids, sarcosinates, taurates and the like. Illustrative examples of these and other classes include sodium lauryl sulfate, sodium coconut monoglyceride sulfonate, sodium lauryl sarcosinate, sodium lauryl isoethionate, sodium laureth carboxylate and sodium dodecyl benzenesulfonate. Suitable nonionic surfactants include without limitation, poloxamers, polyoxyethylene sorbitan esters, fatty alcohol ethoxylates, alkylphenol ethoxylates, tertiary amine oxides, tertiary phosphine oxides, dialkyl sulfoxides and the like. Suitable amphoteric surfactants include without limitation, derivatives of $C_{8-20}$ aliphatic secondary and tertiary amines having an anionic group such as carboxylate, sulfate, sulfonate, phosphate or phosphonate. A suitable example is cocoamidopropyl betaine. One or more surfactants are optionally present in a total amount of about 0.01 wt. % to about 10 wt. %, for example, from about 0.05 wt. % to about 5 wt. %, or from about 0.1 wt. % to about 2 wt. % by total weight of the composition.

In a still further embodiment, the composition of the invention comprises at least one foam modulator, useful for example to increase amount, thickness or stability of foam generated by the composition upon agitation. Any orally acceptable foam modulator can be used, including without limitation, polyethylene glycols (PEGs), also known as polyoxyethylenes. High molecular weight PEGs are suitable, including those having an average molecular weight of 200,000 to 7,000,000, for example 500,000 to 5,000,000, or 1,000,000 to 2,500,000. One or more PEGs are optionally present in a total amount of about 0.1 wt. % to about 10 wt. %, for example from about 0.2 wt. % to about 5 wt. %, or from about 0.25 wt. % to about 2 wt. %, by total weight of the composition.

In a still further embodiment, the composition of the invention comprises at least one thickening agent, useful for example to impart a desired consistency and/or mouth feel to the composition. Any orally acceptable thickening agent can be used, including without limitation, carbomers, also known as carboxyvinyl polymers, carrageenans, also known as Irish moss and more particularly t-carrageenan (iota-carrageenan), cellulosic polymers such as hydroxyethylcellulose, carboxymethylcellulose (CMC) and salts thereof, e.g., CMC sodium, natural gums such as karaya, xanthan, gum arabic and tragacanth, colloidal magnesium aluminum silicate, colloidal silica and the like. A preferred class of thickening or gelling agents includes a class of homopolymers of acrylic acid crosslinked with an alkyl ether of pentaerythritol or an alkyl ether of sucrose, or carbomers. Carbomers are commercially available from B. F. Goodrich as the Carbopol® series. Particularly preferred Carbopols include Carbopol 934, 940, 941, 956, 974P, and mixtures thereof. One or more thickening agents are optionally present in a total amount of from about 0.01 wt. % to 15 wt. %, for example from about 0.1 wt. % to about 10 wt. %, or from about 0.2 wt. % to about 5 wt. %, by total weight of the composition.

In a still further embodiment, the composition of the invention comprises at least one viscosity modifier, useful for example to inhibit settling or separation of ingredients or to promote re-dispersibility upon agitation of a liquid composition. Any orally acceptable viscosity modifier can be used, including without limitation, mineral oil, petrolatum, clays and organomodified clays, silica and the like. One or more viscosity modifiers are optionally present in a total amount of from about 0.01 wt. % to about 10 wt. %, for example, from about 0.1 wt. % to about 5 wt. %, by total weight of the composition.

In a still further embodiment, the composition of the invention comprises at least one humectant. Any orally acceptable humectant can be used, including without limitation, polyhydric alcohols such as glycerin, sorbitol, xylitol or low molecular weight PEGs. Most humectants also function as sweeteners. One or more humectants are optionally present in a total amount of from about 1 wt. % to about 70 wt. %, for example, from about 1 wt. % to about 50 wt. %, from about 2 wt. % to about 25 wt. %, or from about 5 wt. % to about 15 wt. %, by total weight of the composition.

In a still further embodiment, a composition of the invention comprises at least one sweetener, useful for example to enhance the taste of the composition. Any orally acceptable natural or artificial sweetener can be used, including without limitation dextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof, dipeptide-based intense sweeteners, cyclamates and the like. One or more sweeteners are optionally present in a total amount depending strongly on the particular sweetener(s) selected, but typically 0.005 wt. % to 5 wt. %, by total weight of the composition.

In a still further embodiment, the flavorant blend of the composition of the invention may additionally comprise, in addition to the phenyl alkene flavorant, in particular anethole, at least one further flavorant, useful for example to enhance taste of the composition. Any orally acceptable natural or synthetic further flavorant can be used, including without limitation vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants and the like. Also encompassed within flavorants herein are ingredients that provide fragrance and/or other sensory effect in the mouth, including cooling or warming effects. Such ingredients illustratively include menthol, menthyl acetate, menthyl lactate, camphor, eucalyptus oil, eucalyptol, eugenol, cassia, oxanone, α-irisone, propenyl guaiethol, thymol, linalool, benzaldehyde, cinnamaldehyde, N-ethyl-p-menthan-3-carboxamine, N,2,3-trimethyl-2-isopropylbutanamide, 3-(1-menthoxy)-propane-1,2-diol, cinnamaldehyde glycerol acetal (CGA), menthone glycerol acetal (MGA) and the like. One or more flavorants are optionally present in a total amount of from about 0.01 wt. % to about 5 wt. %, for example, from about 0.1 wt. % to about 2.5 wt. %, by total weight of the composition.

In a still further embodiment, the colorant blend of the composition of the invention may comprise at least one additional colorant. Colorants herein include pigments, dyes, lakes and agents imparting a particular luster or reflectivity such as pearling agents. The colorant blend is optionally present in a total amount of from about 0.001 wt. % to about 20 wt. %, for example, from about 0.01 wt. % to about 10 wt. %, or from about 0.1 wt. % to about 5 wt. %, by total weight of the composition.

In some embodiments, the composition comprises a fluoride ion source. Fluoride ion sources include, but are not limited to: stannous fluoride, sodium fluoride, potassium fluoride, potassium monofluorophosphate, sodium monofluorophosphate, ammonium monofluorophosphate, sodium fluorosilicate, ammonium fluorosilicate, amine fluoride such as olaflur (N'-octadecyltrimethylendiamine-N,N,N'-tris(2-ethanol)-dihydrofluoride), ammonium fluoride, and combinations thereof. In certain embodiments the fluoride ion source includes stannous fluoride, sodium fluoride, amine fluorides, sodium monofluorophosphate, as well as mixtures thereof. In certain embodiments, the oral care composition of the invention may also contain a source of fluoride ions or fluorine-providing ingredient in amounts sufficient to supply about 50 to about 5000 ppm fluoride ion, e.g., from about 100 to about 1000, from about 200 to about 500, or about 250 ppm fluoride ion. Fluoride ion sources may be added to the compositions of the invention at a level of about 0.001 wt. % to about 10 wt. %, e.g., from about 0.003 wt. % to about 5 wt. %, 0.01 wt. % to about 1 wt., or about 0.05 wt. %. However, it is to be understood that the weights of fluoride salts to provide the appropriate level of fluoride ion will obviously vary based on the weight of the counter ion in the salt, and one of skill in the art may readily determine such amounts. A preferred fluoride salt may be sodium fluoride.

The composition of the present invention optionally comprises a saliva stimulating agent useful, for example, in amelioration of dry mouth. Any orally acceptable saliva stimulating agent can be used, including without limitation food acids such as citric, lactic, malic, succinic, ascorbic, adipic, fumaric and tartaric acids, and mixtures thereof. One or more saliva stimulating agents are optionally present in saliva stimulating effective total amount.

The composition of the present invention optionally incorporates one or more antisensitivity agents, e.g., potassium salts such as potassium nitrate, potassium bicarbonate, potassium chloride, potassium citrate, and potassium oxalate; capsaicin; eugenol; strontium salts; zinc salts; chloride salts and combinations thereof. Such agents may be added in effective amounts, e.g., from about 1 wt. % to about 20 wt. % by weight based on the total weight of the composition, depending on the agent chosen. The compositions of the present invention may also be used to treat hypersensitivity by blocking dentin tubules when applied to a tooth.

In some embodiments, the composition of the invention further comprises an antioxidant. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

In another embodiment, the composition comprises an orally acceptable zinc ion source useful, for example, as an antimicrobial, anticalculus or breath-freshening agent. One or more such sources can be present. Suitable zinc ion sources include without limitation zinc acetate, zinc citrate, zinc gluconate, zinc glycinate, zinc oxide, zinc sulfate, sodium zinc citrate and the like. One or more zinc ion sources are optionally and illustratively present in a total amount of from about 0.05 wt. % to about 3 wt. %, for example from about 0.1 wt. % to about 1 wt. %, by total weight of the composition.

The compositions may contain additional therapeutic and non-therapeutic components, and may also be utilized in the practice of various methods, all of which are included within the scope of the invention. The composition and methods within the scope of the invention may be useful in, for example, reducing or eliminating tooth sensitivity of a mammal, improving/maintaining systemic health, and/or occluding dentin tubules.

Anti-bacterial agents may be incorporated in the oral care compositions of the invention. Common antibacterial agents used in oral care include triclosan, chlorhexidine, cetyl pyridinium chloride, and other quaternary amines. These agents, when present, are incorporated in the oral care composition in effective amounts that do not substantially adversely affect the desired properties and characteristics of the composition.

The composition of the present invention may additionally optionally comprise a tartar control (anticalculus) agent as provided below. Tartar control agents among those useful herein include salts of the specified agents, including alkali metal and ammonium salts. The agents include: phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof. Other useful tartar control agents include polycarboxylate polymers and polyvinyl methyl ether/maleic anhydride (PVM/MA) copolymers, such as GANTREZ®.

In some embodiments, the composition of the present invention further comprises a nutrient. Suitable nutrients include vitamins, minerals, amino acids, and mixtures thereof. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Nutritional supplements include amino acids (such as L-tryptophan, L-lysine, methionine, threonine, levocarnitine and L-carnitine), lipotropics (such as choline, inositol, betaine, and linoleic acid), and mixtures thereof.

The composition according to the present invention may be administered to or applied to a human or other animal subject. The composition may be suitable for administration or application to the oral cavity of a human or animal subject. Typically, the composition is for treating or reducing oral bacteria, treating, reducing or dissolving plaque, whitening teeth and/or removing tooth stains.

The invention is further illustrated by the following non-limiting Examples.

EXAMPLES

Comparative Example 1

An alcohol-free mouthwash was provided, which included cetyl pyridinium chloride as an anti-bacterial active component. The mouthwash was bright mint green in color and included a colorant blend composed of 0.00040 wt % FD & C Green No. 3 and 0.00072 wt % FD & C Yellow No. 5, consisting of tartrazine, each weight % being based on the total weight of the mouthwash. The mouthwash also included a flavorant blend which included 0.048 wt % trans-anethole based on the total weight of the mouthwash.

The color co-ordinates of the mouthwash were L=85.90, a=−33.3 and b=10.45.

When the mouthwash was exposed to an accelerated aging test comprising ambient daylight conditions and a temperature of 40° C. for a period of 4 weeks, the green color noticeably faded and was readily perceptible to the human eye. The fading was measured, and delta E was 18.22.

Accordingly, the color fade was unacceptably high in the accelerated aging test.

Example 1

The same alcohol-free mouthwash as in Comparative Example 1 was used in Example 1 except that one colorant of the colorant blend was modified.

Again, the mouthwash was bright mint green in color, but in this Example included a colorant blend composed of 0.00040 wt % FD & C Green No. 3 and 0.00072 wt % FD & C Yellow No. 6, each weight % being based on the total weight of the mouthwash. The mouthwash included the same flavorant blend which included 0.048 wt % trans-anethole based on the total weight of the mouthwash. The pH of the mouthwash was 6.50.

The color co-ordinates of the mouthwash were L=73.94, a=−5.28 and b=10.6. The green was slightly less prominent in the overall hue as a result of a less negative color co-ordinate a.

When the mouthwash was exposed to an accelerated aging test comprising ambient daylight conditions and a temperature of 40° C. for a period of 4 weeks, the green color did not perceptibly fade. The delta E was 1.13, representing a color change which is substantially imperceptible to the human eye.

Example 2

The same alcohol-free mouthwash as employed in Example 1 was used except that the colorant blend was further modified with respect to the amounts of the colorants, and also a pH adjuster, comprising citric acid, was added.

Again, the mouthwash was bright mint green in color, but in this Example included a colorant blend composed of 0.00044 wt % FD & C Green No. 3 and 0.00036 wt % FD & C Yellow No. 6, each weight % being based on the total weight of the mouthwash. The mouthwash also included a flavorant blend which included 0.048 wt % trans-anethole based on the total weight of the mouthwash. The citric acid was present in an amount of 0.01 wt % based on the total weight of the mouthwash. The pH of the mouthwash was 5.16.

The color co-ordinates of the mouthwash were L=45.41, a=−13.9 and b=1.4. The green overall hue was, as perceived by the human eye, substantially the same as that of Comparative Example 1.

When the mouthwash was exposed to an accelerated aging test comprising ambient daylight conditions and a temperature of 40° C. for a period of 4 weeks, the green color did not perceptibly fade. The delta E was 1.82, representing a color change which is substantially imperceptible to the human eye.

Accordingly, the Examples and Comparative Example show that changing the colorant blend when the composition comprises a phenyl alkene flavorant can unexpectedly overcome the problem of color fading during extended storage and use of the oral care composition, particularly a mouthwash or mouthrinse.

What is claimed is:

1. An oral care composition comprising:
   a colorant blend comprising a triarylmethane green colorant and a naphthalene sulfonate yellow colorant in a weight ratio of from 2:1 to 1:2; and
   a substituted or unsubstituted phenyl alkene flavorant.

2. The oral care composition of claim 1 wherein the triarylmethane green colorant comprises FD & C Green No. 3 colorant.

3. The oral care composition of claim 1 wherein the naphthalene sulfonate yellow colorant comprises FD & C Yellow No. 6 colorant.

4. The oral care composition of claim 1, wherein the colorant blend provides a green color to the oral care composition.

5. The oral care composition of claim 1 wherein the triarylmethane green colorant and the naphthalene sulfonate yellow colorant are present in a weight ratio of from 1.5:1 to 1:1.5.

6. The oral care composition of claim 4 wherein triarylmethane green colorant and the naphthalene sulfonate yellow colorant are present in a weight ratio of from 1.25:1 to 1:1.

7. The oral care composition of claim 5 wherein the triarylmethane green colorant and the naphthalene sulfonate yellow colorant are present in a weight ratio of about 1.2:1.

8. The oral care composition of claim 1 wherein the triarylmethane green colorant is present in an amount of from 0.00025 to 0.00075 wt % and the naphthalene sulfonate yellow colorant is present in an amount of from 0.00025 to 0.00075 wt %, each based on the total weight of the composition.

9. The oral care composition of claim 7 wherein the triarylmethane green colorant is present in an amount of from 0.00035 to 0.00055 wt % and the naphthalene sulfonate yellow colorant is present in an amount of from 0.00030 to 0.00045 wt %, each based on the total weight of the composition.

10. The oral care composition of claim 8 wherein the triarylmethane green colorant is present in an amount of from 0.00040 to 0.00050 wt % and the naphthalene sulfonate yellow colorant is present in an amount of from 0.00030 to 0.00040 wt %, each based on the total weight of the composition.

11. The oral care composition of claim 1 wherein the substituted or unsubstituted phenyl alkene flavorant comprises an unsaturated phenyl ether.

12. The oral care composition of claim 10 wherein the unsaturated phenyl ether comprises anethole.

13. The oral care composition of claim 1 wherein the substituted or unsubstituted phenyl alkene flavorant is present in a weight ratio of from 8:1 to 4:1 with respect to the colorant blend.

14. The oral care composition of claim 12 wherein the substituted or unsubstituted phenyl alkene flavorant is present in a weight ratio of about 6:1 with respect to the colorant blend.

15. The oral care composition of claim 1 wherein the substituted or unsubstituted phenyl alkene flavorant is present in an amount of from 0.003 to 0.007 wt % based on the total weight of the composition.

16. The oral care composition of claim 14 wherein the substituted or unsubstituted phenyl alkene flavorant is present in an amount of from 0.004 to 0.006 wt % based on the total weight of the composition.

17. The oral care composition of claim 15 wherein the substituted or unsubstituted phenyl alkene flavorant is present in an amount of from 0.0045 to 0.0050 wt % based on the total weight of the composition.

18. The oral care composition of claim 1 further comprising a pH adjuster to adjust the pH of the composition and the pH of the composition is from 4.60 to 5.60.

19. The oral care composition of claim 17 wherein the pH of the composition is about 5.10.

20. The oral care composition of claim 17 wherein the pH adjuster comprises an organic acid.

21. The oral care composition of claim 19 wherein the organic acid is citric acid.

22. The oral care composition of claim 19 wherein the organic acid is present in an amount of from 0.005 to 0.015 wt % based on the total weight of the composition.

23. The oral care composition of claim 21 wherein the organic acid is present in an amount of from 0.008 to 0.012 wt % based on the total weight of the composition.

24. The oral care composition of claim 1 wherein the green color has a delta E of less than 2 when exposed to an accelerated aging test comprising ambient daylight conditions and a temperature of 40° C. for a period of 4 weeks.

25. The oral care composition of claim 1 which is a mouthwash or mouthrinse.

* * * * *